United States Patent [19]

Regan et al.

[11] Patent Number: 5,716,835
[45] Date of Patent: Feb. 10, 1998

[54] NUCLEIC ACID ENCODING A NOVEL HUMAN EP PROSTAGLANDIN RECEPTOR

[75] Inventors: John W. Regan, Tucson, Ariz.; Daniel W. Gil, Corona Del Mar; David F. Woodward, Lake Forest, both of Calif.

[73] Assignee: Allergan, Inc., Irvine, Calif.

[21] Appl. No.: 239,431

[22] Filed: May 5, 1994

[51] Int. Cl.$^6$ ............................................... C12N 15/12
[52] U.S. Cl. ............................. 435/240.2; 435/252.3; 435/254.11; 435/69.1; 536/23.5
[58] Field of Search ................... 536/23.1, 23.5; 435/240.1, 240.2, 254.11, 252.3, 69.1

[56] References Cited

PUBLICATIONS

Bastien, Lison et al.; The Journal of Biological Chemistry; col. 269, No. 16, Apr. 22, pp. 11873–11877, 1994; "Cloning, Functional Expression, and Characterization of the Human Prostaglandin E2 Receptor EP2 Subtype".

1994 Receptor & Ion Channel Nomenclature Supplement; Trends in Pharmacological Sciences; Fifth Edition; p. 6.

An, S. et al., Cloning and expression of the EP2 subtype of human receptors for prostaglandin E2. Biochemical and Biophysical Research Communications 197:263–270 (1993).

Colman, R.A., Eicosanoids and other bioactive lipids in cancer, inflammation and radiation injury. Nigam, S. et al. eds. 135–151 (1991).

Coleman, R.A. et al., A novel inhibitory prostanoid receptor in piglet saphenous vein. Prostaglandins 47:151–168 (1994).

Dong, Y.J. et al., Prostaglandin E receptor subtypes in smooth muscle: agonist activities of stable prostacyclin analogues. Br. J. Pharmacol. 87:97–107 (1986).

Funk, C.D. et al., Cloning and expression of a cDNA for the human prostaglandin E receptor $EP_1$ Subtype. J. Biol. Chem. 268(35):26767–26772 (1993).

Gardiner, P.J., Characterization of prostanoid relaxant/inhibitory receptors using a highly selective agonist, TR4979. Br. J. Pharmacol. 87:45–56 (1986).

Giles, H., More selective ligands at eicosanoid receptor subtypes improve prospects in inflammatory and cardiovascular research. Trends Pharm. Sci. 11:301–304 (1990).

Hébert, R.L. et al., $PGE_2$ inhibits AVP–induced water flow in cortical collecting ducts by protein kinase C activation. Am. J. Physiol. 259:F318–F325 (1990).

Hirata, M. et al., Cloning and expression of cDNA for a human thromboxane $A_2$ receptor. Nature 349:617–620 (1991).

Honda, A. et al., Cloning and expression of a cDNA for mouse prostaglandin E receptor $EP_2$ subtype. J. Biol. Chem. 268(11):7759–7762 (1993).

Humbles, A.A. et al., Pharmacological characterisation of the protanoid receptors in the rabbit isolated ear artery. Br. J. Pharmacol. 108:74P (1993).

Milne, S.A. et al., Furthur investigation of prostanoid EP receptors in rabbit jugular and pig saphenous veins. Br. J. Pharmacol. III:79P (1994).

Nials, A.T. et al., AH13205, a selective prostanoid $EP_2$–receptor agonist. Cardiovascular Drug Reviews 11(2):165–179 (1993).

Regan, J.W. et al., Molecular cloning and expression of human $EP_3$ receptors: evidence of three variants with differing carboxyl termini. Br. J. Pharmacol. 112:377–385 (1994).

Senior, J. et al., In vitro characterization of prostanoid EP–receptors in the non–pregnant human myometreium. Br. J. Pharmacol. 102:747–753 (1991).

Smith, W.L., Prostanoid biosynthesis and mechanisms of action. Am. J. Physiol. 263:F181–F191 (1992).

Sonnenburg, W.K. and Smith, W.L., Regulation of cyclic AMP metabolism in rabbit cortical collecting tubule cells by prostaglandins. J. Biol. Chem. 263(13):6155–6160 (1988).

Sugimoto, Y. et al., Cloning and expression of a cDNA for mouse prostaglandin E receptor $EP_3$ Subtype. J. Biol Chem. 267(10):6463–6466 (1992).

Woodward, D.F. et al., Identification of 19 (R)–OH prostaglandin $E_2$ as a selective prostanoid $EP_2$–receptor agonist. Postaglandins 46:371–383 (1993).

Yeardley, H.L. et al., The effects of spasmolytic and spasmogenic prostanoids on cyclic amp levels in human myometrium from pregnant donors. Br. J. Pharmacol. Proc. Suppl. 108:174p (1992).

Katsuyama et al., FEBS Letters, vol. 344, p. 74, 1994.

*Primary Examiner*—Stephen G. Walsh
*Assistant Examiner*—Sally P. Teng
*Attorney, Agent, or Firm*—Knobbe Martens Olson & Bear, LLP

[57] ABSTRACT

A gene encoding the HP4 human prostaglandin receptor is disclosed. The protein encoded by this gene exhibits significant sequence identity with other prostaglandin receptors. The HP4 receptor, when expressed in eukaryotic cells, is capable of binding prostaglandins and their analogs and stimulating adenylate cyclase activity in response to prostaglandins.

6 Claims, 2 Drawing Sheets

NUCLEIC ACID ENCODING A NOVEL HUMAN EP PROSTAGLANDIN RECEPTOR

FIELD OF THE INVENTION

This invention relates to the cloning and expression of a novel human prostaglandin receptor. Methods of identifying compounds capable of both binding to and activating this receptor are also disclosed. As determined using the disclosed methods, the receptor exhibits $EP_2$ pharmacology.

BACKGROUND OF THE INVENTION

Prostaglandins are a group of hormone mediators derived from the metabolism of arachidonic acid via the cyclooxygenase enzymatic pathway. In the prostaglandin biosynthetic pathway, arachidonic acid is first converted to prostaglandin endoperoxide $H_2$ (PGH2) by PGH2 synthases followed by the cell-specific isomerization or reduction of PGH2 to the active prostaglandins: $PGD_2$, $PGE_2$, $PGF_{2\alpha}$, prostacyclin ($PGI_2$) and thromboxane ($TxA_2$). Following enzymatic conversion, the major biologically active prostaglandins exert their actions locally on the cells in which they were synthesized (autocrine) and/or on nearby cells (paracrine) through specific G protein-coupled receptors (Smith, (1992) *Am. J. Physiol.*, 263: F181–F191) to either stimulate or inhibit the production of second messengers. Prostaglandins elicit a diverse spectrum of often opposing biological effects including muscle contraction and relaxation, potentiation and inhibition of platelet aggregation, and vasodilation and vasoconstriction. Prostaglandins also exhibit both pro-inflammatory and anti-inflammatory effects. They synergize with other pro-inflammatory mediators such as leukotrienes and bradykinins, but attenuate interleukin-1 (IL-1) production and inhibit various aspects of leukocyte function (Giles, (1990) *Trends Pharmacol. Sci.*, 11:301–304).

Prostaglandin $E_2$ ($PGE_2$) exhibits a broad range of actions in a number of tissues by binding to at least four EP receptor subtypes. It acts through pharmacologically distinct stimulatory ($EP_2$) and inhibitory ($EP_3$) receptor subtypes to stimulate and inhibit cyclic AMP (cAMP) formation, respectively (Sonnenburg, and Smith, (1988) *J. Biol. Chem.*, 263: 6155–6160). $PGE_2$ also stimulates calcium release and protein kinase C activity in the rabbit kidney collecting tubule, most likely by binding to the $EP_1$ receptor subtype which is coupled to stimulation of phospholipase C (Hebert et al., (1990) *Am. J. Physiol.*, 259: F318–F325). The $EP_4$ receptor is an additional subtype of $PGE_2$-sensitive receptor that was recently identified based on agonist effects and blockade by the antagonist AH 23848B (Louttit et al., (1992) *The Eighth International Congress on Prostaglandins and Related Compounds*, Montreal, 258; Coleman et al., (1994) *Prostaglandins*, 47:151–168). Other $PGE_2$-sensitive receptors with distinct agonist pharmacology have been described (Milne et al., (1994) *Br. J. Pharmacol.*, 111:79), but it is not clear whether they are different from the $EP_4$ receptor.

Analogs of $PGE_2$ that are therapeutically useful will elicit or block only a subset of its actions by acting on a single EP receptor subtype. Because prostaglandin receptors are present in tissues in low abundance, the discovery of such analogs is facilitated by the cloning of the receptors. Assigning cloned receptors to a corresponding pharmacologically defined binding site is an iterative process. Defining novel subtypes requires selective compounds, which may only be developed once the receptor is cloned.

Three human receptors that bind $PGE_2$ have been cloned. The $EP_1$ (Funk et al., (1993) *J. Biol. Chem.*, 268: 26767–26772) and $EP_3$ (Regan et al., (1994) *Br. J. Phamacol.*, in press) subtypes have been well characterized with subtype-selective compounds, but the pharmacology of the putative $EP_2$ receptor (An et al., (1993) *Biochem. Biophys. Res. Commun.*, 197:263–270; Honda et al., (1993) *J. Biol. Chem.*, 268:7759–7762) is not entirely consistent with the pharmacology derived from tissue models of the $EP_2$ receptor. In particular, the $EP_2$-selective agonist butaprost, is inactive (Gardiner (1986) *Br. J. Pharmacol.*, 87:45–56; Coleman, (1993) in *Eicosanoids and Other Bioactive Lipids in Cancer, Inflammation and Radiation Injury*, Nigan et al., eds., pp. 135–141). The pharmacology of this putative $EP_2$ clone is more similar to that of the $EP_4$ receptor, but it was named before the $EP_4$ receptor had been described.

The deduced protein sequences of the cloned receptors indicate that all are members of the G protein-linked receptor superfamily, having seven putative membrane-spanning hydrophobic domains. The proteins share significant amino acid sequence similarity with other members of this family including the thromboxane (TP) receptor (Hirata et al., (1991) *Nature* 349: 617–620), rhodopsin and the adrenergic receptors.

The cloning of $EP_2$ and/or additional EP receptors will facilitate identification of prostaglandins which can modulate specific effects elicited by this receptor. Since these effects will differ from those activated by other EP receptors, such compounds will have therapeutic utility.

SUMMARY OF THE INVENTION

One embodiment of the present invention is an isolated DNA molecule encoding a novel mammalian prostaglandin EP receptor, herein called HP4 (Human Placental clone Number 4). Preferably, the DNA molecule is human; most preferably, the DNA molecule has the nucleotide sequence shown in SEQ ID NO: 3. According to another aspect of the invention, there is provided an isolated DNA molecule having at least 18 consecutive nucleotides of the DNA molecule encoding the HP4 receptor. In accordance with another aspect of the invention, there is provided an isolated amino acid sequence derived from the HP4 receptor DNA sequence. Preferably, the amino acid sequence is human; most preferably it is SEQ ID NO:4. Advantageously, there is also provided a recombinant construct comprising the HP4 receptor DNA sequence operably linked to a heterologous promoter. In another aspect of this preferred embodiment, there is provided an isolated antibody having binding affinity for the isolated HP4 receptor amino acid sequence. Preferably, the antibody is monoclonal.

Another embodiment of the invention is a method of screening compounds for binding to the prostaglandin HP4 receptor comprising:

transfecting cells with a DNA molecule encoding an HP4 receptor, wherein the DNA molecule is operably linked to a promoter in an expression vector;

culturing the cells to express the HP4 receptor;

incubating at least the cell membranes of the cells in the presence of a labeled compound to be tested for binding affinity to the HP4 receptor; and measuring the amount of label bound to the cell membranes, wherein an increased amount of the label associated with the cell membranes indicates that the compound binds to the receptor.

Preferably, the cells are mammalian; most preferably, they are COS-7 cells. In another aspect of this preferred embodiment, the HP4 receptor is human. Preferably, it is encoded by the polynucleotide of SEQ ID NO:3. Advantageously, the expression vector is mammalian; most preferably, it is pBC12BI. In accordance with this aspect of the invention, the label is radioactive, colorimetric or fluorimetric.

In accordance with another aspect of the invention, there is provided a method of determining the ability of a compound to inhibit ligand binding to the prostaglandin HP4 receptor, comprising:

transfecting cells with a DNA molecule encoding a prostaglandin HP4 receptor, wherein the DNA molecule is operably linked to a promoter in an expression vector;

culturing the cells to express the HP4 receptor;

incubating at least the cell membranes of the cultured cells in the presence of a labeled ligand having binding affinity for the receptor and a test compound; and determining the level of binding of the ligand to the prostaglandin HP4 receptor in the presence of the compound, wherein a lower level of ligand binding in the presence of the compound indicates that the compound binds to the receptor.

Preferably, the cells are mammalian; most preferably, they are COS-7 cells and the HP4 receptor is human. In another aspect of the invention, the HP4 receptor is encoded by the polynucleotide of SEQ ID NO:3. Advantageously, the compound label is radioactive, colorimetric or fluorimetric, the expression vector is mammalian, most preferably pBC12BI, and the ligand is $PGE_2$.

Still another embodiment of the invention is a method for identifying compounds that are agonists of the HP4 prostaglandin receptor, comprising:

transfecting cells with a DNA molecule encoding the HP4 receptor, wherein the DNA molecule is operably linked to a promoter in an expression vector;

preincubating the cells in the presence of a phosphodiesterase inhibitor;

incubating the cells in the presence or absence of a compound to be tested;

lysing the cells; and determining the amount of cyclic AMP produced, wherein an increased amount of cyclic AMP indicates that the compound is an agonist of the receptor Preferably, the cells are mammalian; most preferably, they are COS-7 cells. In another aspect of this preferred embodiment, the HP4 receptor is human. In another particularly preferred embodiment, the HP4 receptor is encoded by the polynucleotide of SEQ ID NO:3. Advantageously, the expression vector is mammalian, most preferably pBC12BI and the phosphodiesterase inhibitor is isobutylmethylxanthine.

According to another aspect of this embodiment, there is provided a cell line in continuous culture expressing the HP4 prostaglandin receptor. Preferably, this HP4 prostaglandin receptor is human; most preferably it is encoded by SEQ ID NO:3. Advantageously, the cells are CHO cells.

BRIEF DESCRIPTION OF THE FIGURES

FIG. 1A compares the displacement of $[^3H]$-$PGE_2$ by the naturally-occurring prostaglandins $PGE_2$, $PGE_1$, $PGD_2$ and $PGF_{2\alpha}$. FIG. 1B depicts competition of $[^3H]$-$PGE_2$ binding by synthetic prostaglandins exhibiting selectivity for the $EP_2$ receptor: A13205, Butaprost, 19(R)-hydroxy $PGE_2$ and 11-deoxy $PGE_1$. FIG. 1C compares the inhibition of radioligand binding by additional PGE analogs 16,16-dimethyl $PGE_2$, MB 28767, sulprostone and $PGE_1$-1-OH. The y-axis indicates the percentage of $[^3H]$-$PGE_2$ specifically bound and the x-axis indicates the concentration of competitor added (log M). Points represent the mean values +/− standard error from three separate experiments, performed in duplicate.

DETAILED DESCRIPTION OF THE INVENTION

Figure 1A:
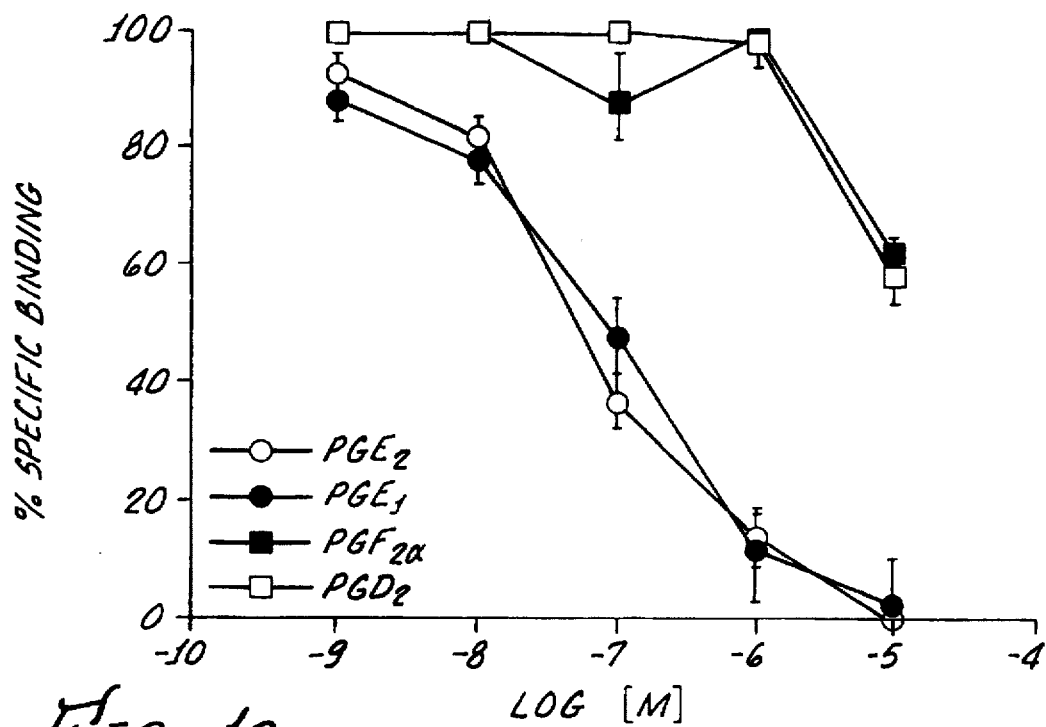
FIGS. 1A, 1B and 1C illustrate competition curves of $[^3H]$-$PGE_2$ binding to COS-7 membranes from COS-7 cells transfected with the HP4 receptor cDNA.

This invention discloses the cloning, sequencing and characterization of a novel human EP prostaglandin receptor, referred to herein as HP4 (Buman Placental clone number 4). To characterize the pharmacology of the prostaglandin receptor of the present invention, the gene was transfected into COS-7 cells which lack prostaglandin receptors and competition binding assays using tritiated $PGE_2$ were performed on the plasma membrane fraction (Sugimoto et al., (1992) *J. Biol. Chem.*, 267: 6463–6466). The results suggest that HP4 is a pharmacologically characterized $EP_2$ receptor.

The HP4 gene sequence, fragments thereof, vectors containing this sequence or unique fragments thereof, cells transfected with this sequence or fragments thereof and protein purified from these cells will be useful for studying the pharmacology and the cellular distribution and expression of the HP4 receptor. Since prostaglandins are known to be involved in a variety of biochemical processes including muscle relaxation, platelet aggregation, vasodilation, and inflammation, the receptor of the present invention will be useful for determining the specific processes mediated by the receptor. Since Northern blot analysis demonstrated that HP4 was expressed at high levels in the lung (Example 5), the receptor of the present invention may be important in the development of treatments for bronchopulmonary inflammation and asthma. Polymerase chain reaction (PCR) amplification of the HP4 sequence indicated that it was present in leukocytes (Example 6), suggesting that it may play an important role in regulating inflammation.

The present invention will also facilitate the identification of compounds which specifically bind to this newly-identified prostaglandin receptor. Since this receptor will mediate responses different from those mediated by the other EP receptor subtypes, these compounds will have utility as therapeutic agents. For example, the $EP_2$-selective agonist AH13205 has been shown to induce bronchodilation and inhibit the release of the inflammatory mediator leukotriene B4 from human neutrophils (Nials et al., (1993) *Cardiovascular Drug Rev.*, 11:165–179). The compound also inhibits the spontaneous contraction of human myometrium (Yeardley et al., (1992) *Br. J. Pharmacol.* Proc. Suppl., 107:90P).

Fragments of the HP4 receptor gene consisting of at least 18 consecutive nucleotides unique to HP4 will be useful as probes and PCR primers for isolating other human prostaglandin receptors, for isolating the corresponding receptor gene from other species and for determining HP4 RNA expression in various human tissues. These oligonucleotides will be useful for in situ hybridization and to probe Northern blots of RNA isolated from various tissues by well known methods to determine the HP4 receptor cellular distribution.

As specific subsets of the prostaglandin receptor family may be involved in different cellular actions, it is important to identify the receptor subtypes expressed by each cell. It can be appreciated that those of ordinary skill in the art could determine unique fragments of the human HP4 receptor and use these fragments as probes to determine cells expressing the desired prostaglandin receptor gene.

In addition, DNA sequences of 18 nucleotides correspond to six amino acids. Those of ordinary skill in the art will appreciate that a six amino acid peptide, when coupled to an immunogenic carrier protein such as keyhole limpet hemocyanin, can be utilized as an antigen to raise antibodies against HP4 receptor epitopes. Alternatively, the HP4 cDNA or fragments thereof can be expressed and the resulting polypeptide recovered and used as an immunogen. Antibodies against the HP4 receptor protein will allow immunohisto-chemical localization of the protein in cells, tissues and body fluids, thereby providing a means for identification of cells expressing the HP4 receptor subtype.

The use of a number of eukaryotic expression vectors is within the scope of the present invention. Those of ordinary skill in the art will appreciate that once the HP4 receptor clone has been identified and sequenced, it can rapidly be incorporated into almost any desired vector. In the present invention, preferable expression vectors are mammalian, with the most preferable vector being pBC12BI. In addition, the use of yeast, baculovirus and prokaryotic expression vectors is also within the scope of the present invention as is the production of HP4 receptors or fragments thereof in these cell types.

Binding assays using the expressed protein, either in whole transfected cells or in membrane preparations, will be particularly useful for identifying HP4 receptor agonists and antagonists. Although the preferred method of identifying receptor ligands is through radiolabeling, other methods known in the art are also within the scope of the present invention. For instance, well known methods exist for colorimetrically and fluorimetrically labeling compounds. One can also measure functional responses in cells expressing the HP4 receptor protein by using signaling systems including, but not limited to, adenylate cyclase, phosphoinositide hydrolysis, guanylate cyclase, ion fluxes and pH changes. These types of response systems can either be present in the host cell or introduced into the host cell along with the receptor. Although the transfected cells of the present invention are mammalian, any cell type able to express a transfected HP4 gene is contemplated. Transient transfection of HP4 into cells is described below; however, production of stable transfectants expressing the HP4 gene using well-known methods is also contemplated (Example 9).

With the gene sequence determined, mutations can now be introduced to study structure-function relationships as they relate to ligand binding and effector system coupling. For example, point mutations can be introduced into the receptor at various locations by well-known methods. The mutant receptor can then be introduced into cells and the effect of the mutation on ligand binding and signaling pathways can be determined. This analysis will indicate which amino acid residue(s) are involved in ligand binding and effector system coupling, helping to differentiate the functions of EP receptor subtypes, and facilitating the discovery of drugs specific for the HP4 receptor. As a first step in isolating the HP4 receptor gene, a human placental cDNA library was screened under low stringency hybridization conditions with the full-length coding sequence of the human $EP_3$ receptor gene as described in the following example. This gene is described in U.S. patent application Ser. No. 08/155,005, filed Nov. 19, 1993, which is hereby incorporated by reference.

EXAMPLE 1

Cloning of the human HP4 receptor by low stringency hybridization

DNA encoding the complete coding sequence of the human $EP_3$ receptor was labeled with $[^{32}P]$-dATP using a nick-translation kit (Gibco-BRL, Gaithersburg, MD) and used to screen a λgt11 human placenta cDNA library (Clontech, Palo Alto, Calif.) by plaque hybridization analysis. The library was plated using $E.$ $coli$ Y1090R$^-$ cells at a density of approximately 25,000 plaques per plate. A total of 16 plates (400,000 plaques) were used from which impressions were taken using nylon membranes (Colony Plaque Screen, DuPont/NEN). DNA was denatured in 0.5M NaOH, 1.5M NaCl, neutralized in 0.5M Tris-HCl, pH 8.0, 1.5M NaCl and baked at 80° C. for 2 hours. Filters were prehybridized for 2 hours at 37° C. in 50% deionized formamide, 1% sodium dodecyl sulfate (SDS), 1M NaCl, 100 μg/ml sonicated, boiled herring sperm DNA. The $^{32}$P-labeled probe (1×10$^6$ cpm) was added and the filters were hybridized at 37° C. overnight. The filters were then washed for 1 hour at 45° C. in 1 X standard saline citrate (SSC), 0.1% SDS, air-dried and exposed to Kodak XAR film (Eastman-Kodak, Rochester, NY) overnight at −70° C.

Polymerase chain reaction (PCR) using primers complementary to λgt11 sequences flanking the cDNA insert region (5'-GACTCCTGGAGCCG-3'; SEQ ID NO:1 and 5'-CGCGGCCAGCGATGG-3'; SEQ ID NO:2) and restriction analysis were used to amplify seven related clones which were placed into three groups based on their size. One member of each group was subcloned into the EcoRI site of pBluescript (Stratagene, La Jolla, Calif.) and its nucleotide sequence determined using the dideoxy chain termination method (United States Biochemical, Cleveland, Ohio). The clones contained overlapping nucleotide sequences. One clone, designated HP4, contained a 2296 nucleotide insert (SEQ ID NO:3) having 156 nucleotides of 5'-untranslated sequence, an open reading frame of 1074 nucleotides encoding a protein of 358 amino acids and 1066 nucleotides of 3'-untranslated sequence. The below-referenced KS/HP4 plasmid has been deposited with the American Type Culture Collection and assigned Accession No. 97472.

The HP4 deduced amino acid sequence was found to have seven hydrophobic putative membrane-spanning domains characteristic of G protein-coupled receptors. The HP4 sequence was aligned with the various putative intracellular loops, extracellular loops, transmembrane domains, and carboxy terminal regions of the thromboxane (TP), $EP_1$, $EP_2$ and $EP_3$ receptors. The alignment revealed a number of conserved residues present in the aligned sequences. In particular, characteristic prostaglandin receptor sequences in the second extracellular loop and seventh transmembrane domain indicated that the isolated HP4 receptor was a prostaglandin receptor. The overall sequence identity of the putative transmembrane regions of HP4 with those of other prostaglandin receptors is 34% for human $EP_{3A}$, 38% for murine $EP_2$, 37% for murine $EP_1$ and 31% for human TP. Thus, although HP4 possesses conserved sequence motifs found in these previously identified receptors, it is clearly distinct.

A vector for the expression of HP4 in eukaryotic cells was made as follows. PCR was used to amplify nucleotides 124–387 of KS/HP4 (the pBluescript HP4 clone). The primers used were 5'-GATGAGCTCTTTAAAA-GGAGGGCGCATCTCTTTTCCAGG-3' (sense; SEQ ID NO:5) and 5'-GGTGAACACCAGCTCGGT-3' (antisense; SEQ ID NO:6). The PCR product was digested with SacI and ligated to the large fragment remaining from the digestion of KS/HP4 with SacI. *E. coli* cells were transformed and a plasmid with a complete open reading frame in the sense orientation was isolated. The latter was digested with DraI and ligated to the pBC12BI expression vector which had been cleaved with BamHi and HindIII and filled in with the large fragment of DNA polymerase I. *E. coli* cells were transformed and a plasmid (pBC/HP4) was isolated in which the DraI site adjacent to nucleotide 124 in HP4 was ligated to the HindIII site (nucleotide 314 in pBC12BI). This orientation placed the coding sequences of HP4 (nucleotides 157–1230) downstream (3') of the rous sarcoma virus promoter in pBC12BI. The final construct, therefore, contained 33 bases of HP4 5'-untranslated sequence, the coding region, and 15 bases of 3'-untranslated sequence.

So as to perform the necessary binding assays for demonstrating the ligand specificity of the protein derived from the isolated clone, the HP4 receptor was expressed in transfected COS-7 cells as described in the following example.

EXAMPLE 2

Expression of the human HP4 receptor in COS-7 cell

Monolayers of COS-7 cells (ATCC CRL 1651; 70–80% confluent) were rinsed with Phosphate Buffered Saline (PBS, Ca/Mg-free) in 150×25 mm culture dishes. Ten ml transfection mix, consisting of 5 µg/ml plasmid DNA and 0.5 mg/ml DEAE-dextran in PBS, was added to each dish and cells were incubated for 30 min at 37° C. Nine ml of the solution was removed from each dish followed by the addition of 10 ml of 100 mM chloroquine in Dulbecco's Modified Eagle Medium (DMEM)/5% fetal bovine serum (FBS). The cells were incubated for 2.5 hr at 37° C., the solution aspirated and 10 ml of 10% dimethyl sulfoxide (DMSO) in DMEM/5% FBS was added. After a 2.5 minute incubation at 37° C., the solution was aspirated and 30 ml DMEM/5% FBS was added. The cells were incubated at 37° C. with media changes at 24 and 48 hours. After 72 hours, the media was aspirated and the cells were scraped into cold TME buffer (50 mM Tris-HCl, pH 7.4, 10 mM MgCl$_2$, 1 mM EDTA). The dishes were rinsed with cold TME buffer and the cells combined and placed on ice.

To demonstrate the binding of EP receptor ligands to isolated membranes of COS-7 cells expressing the HP4 receptor, membranes were isolated and the binding of radiolabeled ligands was assessed in the presence of increasing concentrations of unlabeled prostaglandin receptor agonists as described in the following example.

EXAMPLE 3

COS-7 membrane preparation and radioligand binding assay

Transfected COS-7 cells were homogenized for 30 seconds at approximately 80% power with a Brinkman PT 10/35 Polytron homogenizer. The resulting homogenate was centrifuged at 19,000 rpm for 20 minutes at 4° C. using a Sorvall SS-34 rotor. The membrane pellet was resuspended in cold TME buffer (1 ml per original dish), frozen in liquid nitrogen and stored at −80° C.

Membrane pellets were then diluted in ice-cold 50 mM Tris-HCl buffer at pH 7.4 using a sonicator set at 50 watts. Membrane suspensions (100 µl) were then added to each assay tube to start the binding reaction. Final concentrations of the competition assay were as follows: [$^3$H]-PGE$_2$, 5 nM; 100 µg protein/tube in a total volume of 200 µl. Increasing concentrations of compounds to be tested for competitively inhibiting [$^3$H]-PGE$_2$ binding were incubated for 60 minutes at room temperature. Contents were aspirated onto a presoaked ice-cold Whatman GF/B filter using a Brandel Cell Harvester and washed three times with ice-cold assay buffer. The filters were dried, placed in scintillation fluid and counted.

Figure 1B:
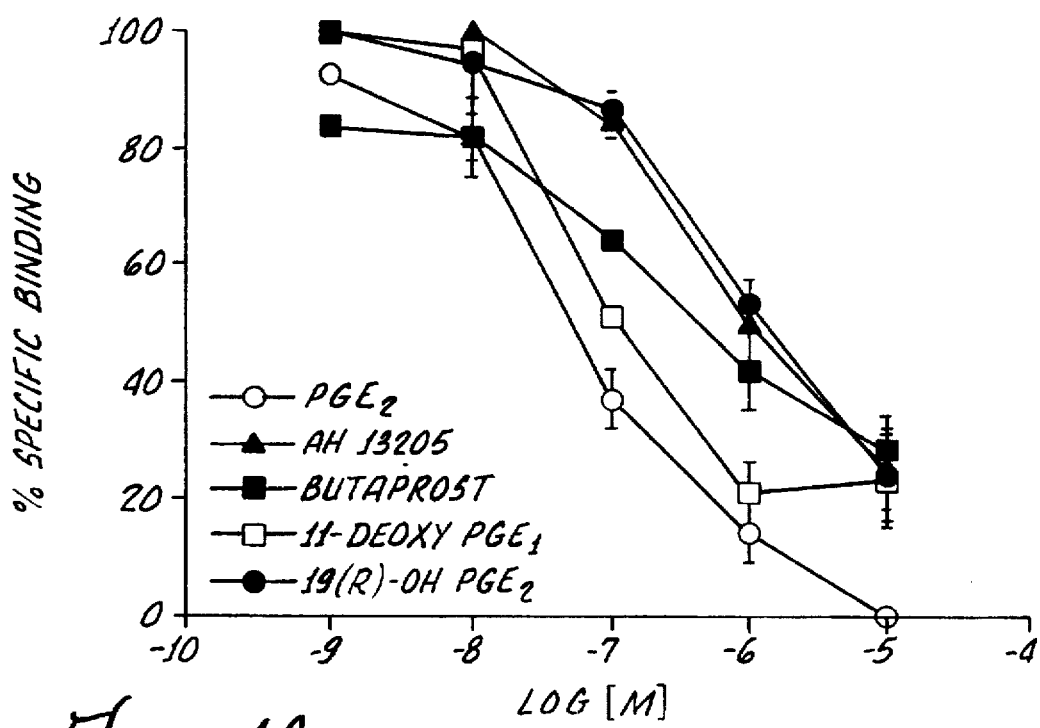

As shown in FIG. 1A, the strongest competitors of [$^3$H]-PGE$_2$ binding were PGE$_2$ itself and PGE$_1$, indicating that the HP4 receptor is in the EP receptor class. Two highly selective agonists for the EP$_2$ receptor, AH13205 and butaprost (Coleman, 1993; Nials et al., 1993; Gardiner, 1986), displaced [$^3$H]-PGE$_2$ binding (FIG. 1B).

Figure 1C:
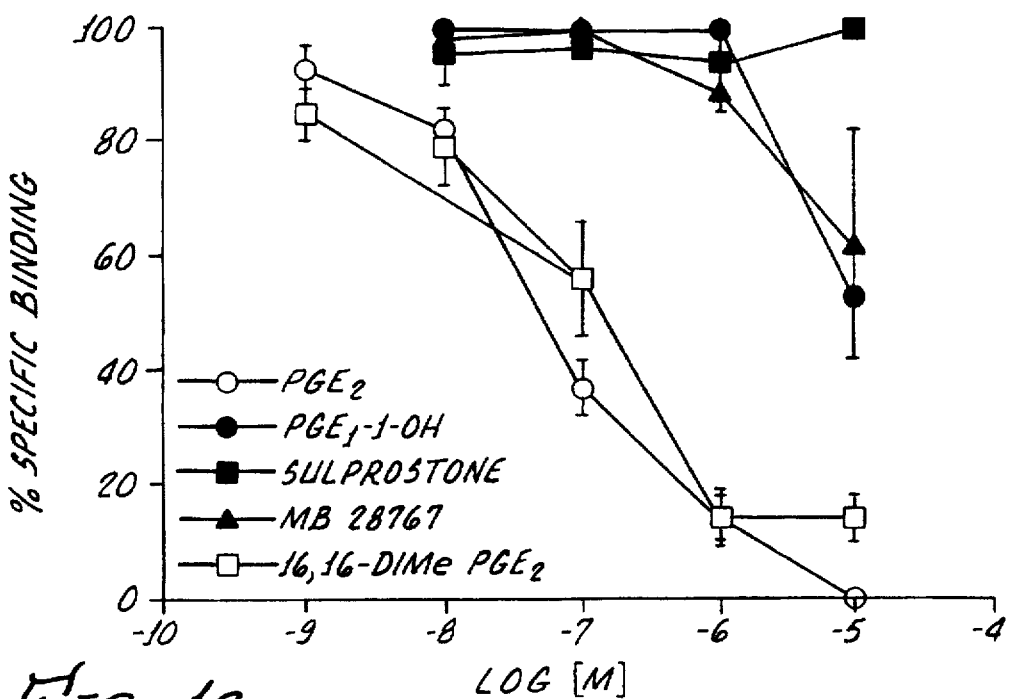

The inhibitory potency of AH13205 relative to PGE$_2$ is very similar to their relative potencies in isolated smooth muscle preparations (Nials et al., 1993; Coleman et al., 1994) 19(R)-hydroxy PGE$_2$ and 11-deoxy PGE$_1$, two additional prostanoids reported to exhibit some degree of selectivity for the EP$_2$ receptor (Woodward et al., (1993) *Prostaglandins*, 46:371–383; Dong et al., (1986) *Br. J. Pharmacol.*, 87:97–107), also exhibited competitive activity (FIG. 1B). FIG. 1C shows that the EP$_3$-selective agonist MB 28767, was only slightly active, as was PGE$_1$-1-OH. Sulprostone, an agonist at both the EP$_1$ and EP$_3$ receptors (Coleman, (1993)), was inactive. 16,16-dimethyl PGE$_2$, which stimulates the EP$_4$ receptor in the rabbit jugular vein (Milne et al., 1994), was active. These results are consistent with the HP4 receptor being the pharmacologically defined EP$_2$ receptor rather than the cloned receptors that were previously designated EP$_2$ (An et al., 1993; Honda et al., 1993). However, identity of HP4 with the EP$_4$ receptor or an additional EP receptor cannot be ruled out.

The native EP$_2$ receptor is coupled through a G protein to the stimulation of adenylate cyclase, an enzyme which transiently associates with the G protein upon prostaglandin binding and converts ATP to cAMP. To determine whether the cloned HP4 receptor could bind prostaglandins and mediate changes in cAMP levels, the HP4 cDNA was transfected into COS-7 cells as described in Example 2. The effect of PGE$_2$ and prostaglandin analogs on cAMP accumulation is described in the following example.

EXAMPLE 4

PGE$_2$ treatment and cAMP assay on HP4-transfected COS cells

HP4-transfected COS-7 cells, prepared as described in Example 2, were cultured in DMEM containing 10% FCS, 100 units/ml penicillin, 100 µg/ml streptomycin. Cells were plated in 24 well plates (Falcon Labware, approximately 2 cm$^2$/well) 24 hours after transfection. Cells were trypsinized and resuspended in a small volume of medium (2–3 ml), counted using a hemocytometer and diluted to 7–8×10$^4$ cells/ml (DMEM/5% FCS). One ml cell suspension was added to each well. After 24 hours at 37° C., the medium was changed and on the following day, cells were rinsed briefly with 1 ml of serum-free medium and were pre-incubated for 1 minute with 400 µl/well of serum-free medium containing 100 µg/ml isobutylmethylxanthine (IBMX), an inhibitor of phosphodiesterase, an enzyme which degrades cAMP. One hundred μl of the indicated concentrations (FIG. 2) of PGE$_2$ or prostaglandin analogs were added to each well for 3 minutes at 37° C. Drug solutions were aspirated and 150 μl TE solution (50 mM Tris-HCl, pH 7.5, 4 mM EDTA) was added. Cells were scraped into TE, boiled for 5 min. in microcentrifuge tubes and placed on ice. Samples were then centrifuged for 10 min at 14,000 rpm to obtain a clarified cytosolic fraction. The amount of cAMP was quantified as follows. Assay standards of 0, 0.125, 0.25, 0.5, 1, 2, 4, 8, 16, 32 and 64 pmol cAMP were prepared by diluting 2X concentrations 1:1 with TE. Fifty μl assay standard or cytosol was then combined with 50 μl [$^3$H]-cAMP. One hundred μl (6 μg) protein kinase A (PKA), an enzyme which binds cAMP, was then added to each tube. One control tube received no PKA, only 100 μl 0.1% BSA/Tris. Samples were vortexed, placed on ice for two hours and 100 μl 2% BSA-2.6% charcoal suspension was added which will bind the PKA-cAMP complex, but not the free cAMP. Samples were vortexed, centrifuged for 45 seconds, placed on ice and 200 μl supernatant transferred to scintillation vials for counting. Counts in the drug-treated samples were compared to counts in the standard tubes to determine the amounts of cAMP. More [$^3$H]-cAMP remaining in the supernatant indicates that more cAMP was synthesized in response to the drug and competitively inhibits binding of the labeled cAMP to PKA.

Figure 2:
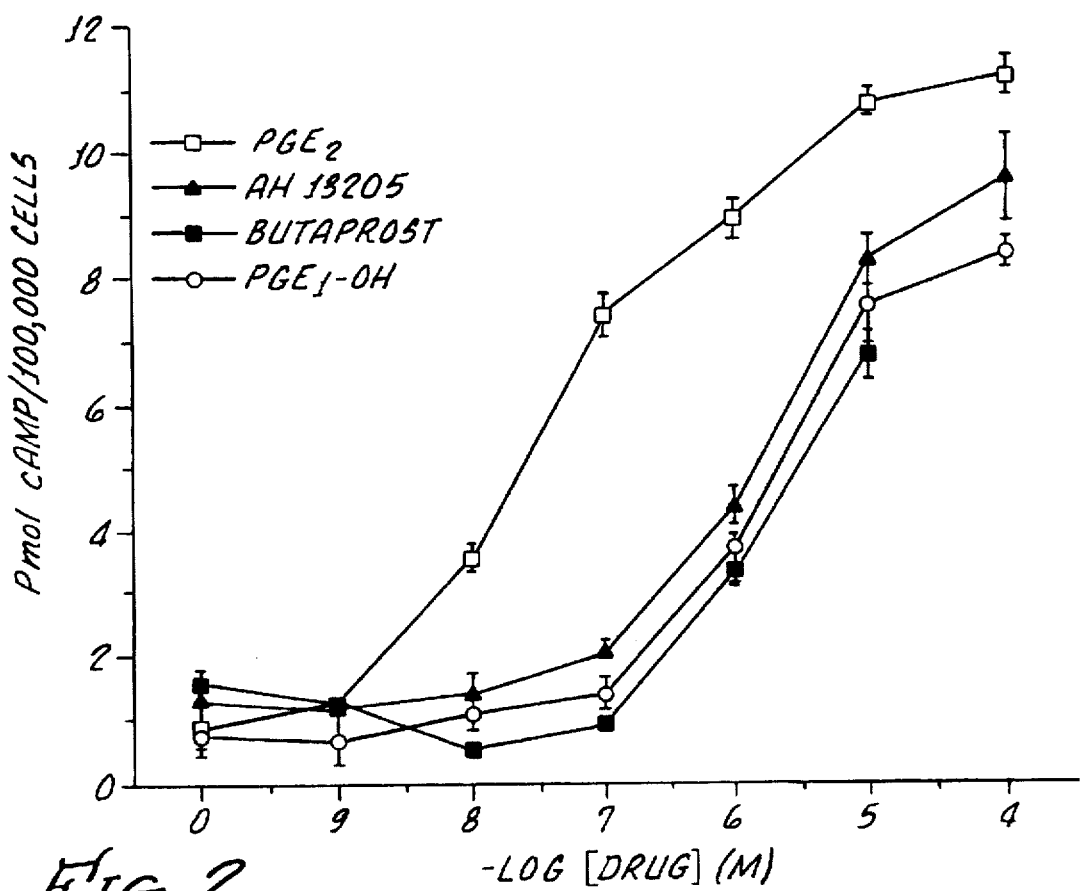
FIG. 2 shows the effects of prostaglandin treatment on cAMP levels in COS-7 cells, after transient transfection with DNA encoding the human HP4 receptor. Subsequent to transfection, cells were stimulated with either $PGE_2$, AH13205, butaprost or $PGE_1$-1-OH. The drug concentration (−log M) is shown on the x-axis and the amount of cAMP produced (pmol/$10^5$ cells) is shown on the y-axis.

The results indicated that PGE$_2$ treatment resulted in significantly increased cAMP levels in HP4-transfected COS cells (FIG. 2). PGE$_2$ could potently stimulate cAMP formation followed by AH13205, butaprost and PGE$_1$-1-OH, in decreasing order of potency. These results are similar to the results obtained in the radioligand binding studies and lend further support to the pharmacological similarity of HP4 with the pharmacologically defined EP$_2$ subtype.

The expression of HP4 mRNA in various human tissues was then determined as described below.

EXAMPLE 5

Tissue distribution of the HP4 prostaglandin receptor gene

A multiple human tissue Northern blot (Clontech, Palo Alto, Calif.) consisting of RNA isolated from heart, brain, placenta, lung, liver, kidney and pancreas was prehybridized in 4.4×SSPE, 44% deionized formamide, 8.8×Denhardt's solution, 1.75% SDS and 88 μg/ml denatured herring sperm DNA at 42° C. with constant rotation. The prehybridization solution was removed and the filter was incubated in fresh solution containing 1.5×10$^6$ cpm/ml nick-translated HP4 cDNA prepared with a kit (Gibco BRL, Gaithersburg, Md.) at 42° C. overnight with constant rotation. The blot was washed six times in 2×SSC, 0.5% SDS at room temperature for 5 minutes each with constant agitation. The blot was then washed in 0.1×SSC, 0.1% SDS at 50° C. for 40 minutes with one change of solution, dried and exposed to x-ray film. The lanes containing the placenta and lung RNA were strongly positive. Since this receptor is expressed at high levels in the lung, it may play a role in regulating airway opening and inflammation in respiratory disorders such as asthma and emphysema.

Because the human uterus (Senior et al., (1991) *Br. J. Pharmacol.*, 102:747-753) and human neutrophils (Nials et al., 1993) are EP$_2$-active tissues, as well as the lung, PCR amplification of RNA was then performed to determine whether HP4 was expressed in human uterus, human placenta, human promyelocytic leukemia HL60 cells (ATCC CCL 240) and/or human acute T-cell leukemia Jurkat T-cells (ATCC TIB 152) as described below.

EXAMPLE 6

PCR amplification of HP4 from human cells and tissues

Sense (5'-CTTACCTGCAGCTGTACG-3'; SEQ ID NO:7) and antisense (5'-GATGGCAAAGACCCAAGG-3'; SEQ ID NO:8) primers corresponding to the second extracellular loop and the seventh transmembrane region, respectively, of the human HP4 receptor clone were used in PCR reactions. Control sense (5'-ATCTGGCACCACACCTTCTACAATGAGCTGCG-3'; SEQ ID NO:9) and antisense (5'-CGTCATACTCCTGCTTGCTGATCCACATCTGC; SEQ ID NO:10) primers to β-actin were also used. RNA was isolated from tissues and cell lines by techniques well known in the art.

The reverse transcription (RT) reaction contained 23 μl water, 2 μl denatured total RNA (1μg/μl, predigested with DNase), 6 μl 10X buffer (Boehringer Mannheim, Ind., Ind.), 12 μl MgCl$_2$ (25 mM), 6 μl dNTPs (10 mM each), 6 μl poly(dN)$_6$ (0.04 OD$_{260}$ units/μl), 0.6 μl acetylated BSA (Promega, 10 mg/ml), 2 μl RNase inhibitor (Boehringer Mannheim, 50 units/μl), 2.4 μl AMV reverse transcriptase (Boehringer Mannheim, 25 units/μl) in a final volume of 60 μl. The reactions were incubated at room temperature for 10 min., 42° C. for 1 hour, 95° C. for 5 min., and held on ice.

The PCR reactions contained 1 μl of the RT reaction, 36.5 μl water, 5 μl 10X buffer (Perkin-Elmer, Norwalk, Conn.), 3 μl MgCl$_2$ (25 mM), 2 μl dNTPs (1.25 mM each), 1 μl tetramethyl ammonium chloride (TMA; 2.5 mM), 0.625 μl sense primer (25 μM), 0.625 μl antisense primer (25 μM), 0.25 μl Taq polymerase (Perkin-Elmer, 5 units/μl) in a final volume of 50 μl. The denaturation step was performed at 94° C. for 2 min, followed by 35–40 cycles at 94° C. for 15 sec, 60° C. for 15 sec and 72° C. for 2 min. A 6 min incubation at 72° C. completed the reaction.

Half of the PCR reactions (25 μl) were analyzed by electrophoresis on a 1.5% agarose gel and staining with ethidium bromide. These samples were run in parallel with positive controls using plasmid DNA as a template and negative controls which did not contain a DNA template. A fragment having the predicted molecular weight based on the HP4 sequence (368 base pairs) was observed in RNA isolated from placenta, uterus, HL 60 cells and Jurkat T-cells. No fragments were amplified in the absence of a DNA template. The HP primers do not amplify a product from human genomic DNA, probably because there is an intron in between the two primers. Thus, the PCR products reflect the presence of mRNA encoding HP4 and not of contaminating genomic DNA.

To estimate the relative level of HP expression from these sources, the same cDNAs were amplified for 25–30 cycles using the actin primers, SEQ ID NOS:9 and 10. Comparison of the product yields with actin and HP primers shows that HP4 is expressed in human uterus, placenta and HL-60 cells, but only at low levels in Jurkat T-cells. Thus, this receptor may also regulate inflammatory processes in disorders such as emphysema and arthritis.

To further characterize the human HP4 receptor, polyclonal antibodies are generated as described in the following example.

EXAMPLE 7

Production of polyclonal antibodies against the human HP4 receptor

PCR primers are used to amplify an approximately 126 nucleotide region corresponding to the hydrophilic amino acid segments connecting the fifth and sixth membrane spanning domains of the human HP4 receptor. The resulting PCR product is purified by agarose gel electrophoresis, cloned into an expression plasmid such as pGEX (Pharmacia, Piscataway, N.J.) and used to transform *E. coli* by standard procedures. The positive clones are identified and induced to express the fusion protein, which is purified by well known methods.

The purified fusion protein is injected into the breast muscle of chickens (50–100 µg/injection) with booster injections given at two week intervals. The IgY antibodies are purified from the egg yolks by well known methods and their specificity determined by immunoblotting of tissue extracts.

In addition, monoclonal antibodies to the human HP4 receptor can be prepared as discussed below.

EXAMPLE 8

Production of monoclonal antibodies against the human HP4 receptor

The HP4 receptor-transfected COS-7 cell lysate, isolated as described in Example 7,is centrifuged to isolate membranes. The isolated membranes are injected in Freund's complete adjuvant into mice. After 9 booster injections over a three week period, the spleens are removed and resuspended in PBS. The resuspended spleen cells are mixed (approximately 4:1) with SP2/0 myeloma cells. Polyethylene glycol is added to fuse the myeloma and spleen cells, and the hybridomas are selected in HAT medium. The fused cells are aliquoted to allow growth of only one cell in each well of a 96 well microtiter plate. Each cell is expanded, the media removed and secreted proteins are labeled with $^{125}$I. The labeled media from each well is used to probe a Western blot of transfected and untransfected COS-7 cell membranes.

The desired hybridoma produces a monoclonal antibody that strongly binds a protein band in a transfected COS-7 cell membrane lane on a Western blot, but does not bind to any other protein in that lane or in an untransfected COS-7 cell membrane lane (control). This method can be used to detect those cells expressing the human HP4 receptor.

EXAMPLE 9

Production of stably-transfected cells

To produce CHO cells stably transfected with the human HP4 gene, CHO cells are cotransfected with 10–30 µg human HP4 and 1–5 µg pSV2Neo carrying the neomycin resistance gene by calcium phosphate precipitation (Graham and Van der Eb, (1973) Virology, 52: 456–467). The cells are then subjected to selection with 600 µg/ml genetecin (G418; Gibco). The resistant colonies are selected, expanded and screened for receptor expression using [$^3$H]-PGE$_2$ binding as described in Example 3 .

A murine homolog of the human HP4 prostaglandin receptor gene is isolated as described below.

EXAMPLE 10

Isolation of a murine HP4 prostaglandin receptor gene

The HP4 gene, isolated as described in Example 1, is digested with restriction enzymes by well-known methods to obtain a DNA segment of approximately 1–1.5 kilobases. This segment is nick-translated using a kit (Gibco BRL, Gaithersburg, Md.) and [$^{32}$P]-dATP, then used to screen mouse cDNA libraries which are available from several commercial sources including Clontech (Palo Alto, Calif.). The positive clones are sequenced and aligned with the HP4 sequence using one of a number of computer sequence alignment programs well-known in the art to determine whether the mouse clone shares significant sequence identity with human HP4 .

While particular embodiments of the invention have been described in detail, it will be apparent to those skilled in the art that these embodiments are exemplary, rather than limiting, and the true scope of the invention is that defined in the following claims.

---

What is claimed is:

1. An isolated DNA molecule encoding a human HP4 prostaglandin receptor, having the amino acid sequence as set forth in SEQ ID NO:4.

2. The DNA molecule of claim 1, wherein said molecule has the nucleotide sequence shown in SEQ ID NO:3.

3. A transfected cell growing in culture, said transfected cell containing an expression vector encoding a recombinant HP4 prostaglandin, having the amino acid sequence as set forth in SEQ ID NO:4.

4. The cell line of claim 3, wherein said HP4 prostaglandin receptor is encoded by a polynucleotide having the sequence shown in SEQ ID NO:3.

5. The transfected cell claim 3, wherein said transfected cell is a transfected CHO cell.

6. The transfected cell of claim 3, wherein the transfected cell is a transiently transfected cell.

* * * * *

UNITED STATES PATENT AND TRADEMARK OFFICE
CERTIFICATE OF CORRECTION

PATENT NO.  : 5,716,835
DATED       : Feb. 10, 1998
INVENTOR(S) : John W. Regan, et al It is certified that error appears in the above-identified patent and that said Letters Patent is hereby corrected as shown below:

Column 23, line 13, claim 1, "luman" should read --human--

Signed and Sealed this

Thirty-first Day of August, 1999

Attest:

Q. TODD DICKINSON

Attesting Officer

Acting Commissioner of Patents and Trademarks

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:1:

GACTCCTGGA GCCG ( 2 ) INFORMATION FOR SEQ ID NO:2:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:2:

```
CGCGGCCAGC GATGG                                                                              15
```

( 2 ) INFORMATION FOR SEQ ID NO:3:

( i ) SEQUENCE CHARACTERISTICS:
        ( A ) LENGTH: 2296 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( i x ) FEATURE:
        ( A ) NAME/KEY: Coding Sequence
        ( B ) LOCATION: 157...1230
        ( D ) OTHER INFORMATION:

( x i ) SEQUENCE DESCRIPTION: SEQ ID NO:3:

```
GGGCCGCCGT CGGCGCGCTG GGTGCGGGAA GGGGGCTCTG GATTTCGGTC CCTGGGGTTT          60

TTCCTCTGAG TCTCGGAACG CTCCAGCTCT CAGACCCTCT TCCTCCCAGG TAAAGGCCGG         120

GAGAGGAGGG CGCATCTCTT TTCCAGGCAC CCCACC ATG GGC AAT GCC TCC AAT          174
                                         Met Gly Asn Ala Ser Asn
                                          1               5

GAC TCC CAG TCT GAG GAC TGC GAG ACG CGA CAG TGG CTT CCC CCA GGC          222
Asp Ser Gln Ser Glu Asp Cys Glu Thr Arg Gln Trp Leu Pro Pro Gly
             10                  15                  20

GAA AGC CCA GCC ATC AGC TCC GTC ATG TTC TCG GCC GGG GTG CTG GGG          270
Glu Ser Pro Ala Ile Ser Ser Val Met Phe Ser Ala Gly Val Leu Gly
         25                  30                  35

AAC CTC ATA GCA CTG GCG CTG CTG GCG CGC CGC TGG CGG GGG GAC GTG          318
Asn Leu Ile Ala Leu Ala Leu Leu Ala Arg Arg Trp Arg Gly Asp Val
     40                  45                  50

GGG TGC AGC GCC GGC CGC AGG AGC TCC CTC TCC TTG TTC CAC GTG CTG          366
Gly Cys Ser Ala Gly Arg Arg Ser Ser Leu Ser Leu Phe His Val Leu
 55                  60                  65                  70

GTG ACC GAG CTG GTG TTC ACC GAC CTG CTC GGG ACC TGC CTC ATC AGC          414
Val Thr Glu Leu Val Phe Thr Asp Leu Leu Gly Thr Cys Leu Ile Ser
                     75                  80                  85

CCA GTG GTA CTG GCT TCG TAC GCG CGG AAC CAG ACC CTG GTG GCA CTG          462
Pro Val Val Leu Ala Ser Tyr Ala Arg Asn Gln Thr Leu Val Ala Leu
```

```
                        90                       95                        100
GCG  CCC  GAG  AGC  CGC  GCG  TGC  ACC  TAC  TTC  GCT  TTC  GCC  ATG  ACC  TTC       510
Ala  Pro  Glu  Ser  Arg  Ala  Cys  Thr  Tyr  Phe  Ala  Phe  Ala  Met  Thr  Phe
          105                      110                      115

TTC  AGC  CTG  GCC  ACG  ATG  CTC  ATG  CTC  TTC  GCC  ATG  GCC  CTG  GAG  CGC       558
Phe  Ser  Leu  Ala  Thr  Met  Leu  Met  Leu  Phe  Ala  Met  Ala  Leu  Glu  Arg
     120                      125                      130

TAC  CTC  TCG  ATC  GGG  CAC  CCC  TAC  TTC  TAC  CAG  CGC  CGC  GTC  TCG  CGC       606
Tyr  Leu  Ser  Ile  Gly  His  Pro  Tyr  Phe  Tyr  Gln  Arg  Arg  Val  Ser  Arg
135                           140                      145                     150

TCC  GGG  GGC  CTG  GCC  GTG  CTG  CCT  GTC  ATC  TAT  GCA  GTC  TCC  CTG  CTC       654
Ser  Gly  Gly  Leu  Ala  Val  Leu  Pro  Val  Ile  Tyr  Ala  Val  Ser  Leu  Leu
                         155                      160                      165

TTC  TGC  TCG  CTG  CCG  CTG  CTG  GAC  TAT  GGG  CAG  TAC  GTC  CAG  TAC  TGC       702
Phe  Cys  Ser  Leu  Pro  Leu  Leu  Asp  Tyr  Gly  Gln  Tyr  Val  Gln  Tyr  Cys
               170                      175                      180

CCC  GGG  ACC  TGG  TGC  TTC  ATC  CGG  CAC  GGG  CGG  ACC  GCT  TAC  CTG  CAG       750
Pro  Gly  Thr  Trp  Cys  Phe  Ile  Arg  His  Gly  Arg  Thr  Ala  Tyr  Leu  Gln
          185                      190                      195

CTG  TAC  GCC  ACC  CTG  CTG  CTG  CTT  CTC  ATT  GTC  TCG  GTG  CTC  GCC  TGC       798
Leu  Tyr  Ala  Thr  Leu  Leu  Leu  Leu  Leu  Ile  Val  Ser  Val  Leu  Ala  Cys
     200                      205                      210

AAC  TTC  AGT  GTC  ATT  CTC  AAC  CTC  ATC  CGC  ATG  CAC  CGC  CGA  AGC  CGG       846
Asn  Phe  Ser  Val  Ile  Leu  Asn  Leu  Ile  Arg  Met  His  Arg  Arg  Ser  Arg
215                           220                      225                     230

AGA  AGC  CGC  TGC  GGA  CCT  TCC  CTG  GGC  AGT  GGC  CGG  GGC  GGC  CCC  GGG       894
Arg  Ser  Arg  Cys  Gly  Pro  Ser  Leu  Gly  Ser  Gly  Arg  Gly  Gly  Pro  Gly
                         235                      240                      245

GCC  CGC  AGG  AGA  GGG  GAA  AGG  GTG  TCC  ATG  GCG  GAG  GAG  ACG  GAC  CAC       942
Ala  Arg  Arg  Arg  Gly  Glu  Arg  Val  Ser  Met  Ala  Glu  Glu  Thr  Asp  His
               250                      255                      260

CTC  ATT  CTC  CTG  GCT  ATC  ATG  ACC  ATC  ACC  TTC  GCC  GTC  TGC  TCC  TTG       990
Leu  Ile  Leu  Leu  Ala  Ile  Met  Thr  Ile  Thr  Phe  Ala  Val  Cys  Ser  Leu
     265                      270                      275

CCT  TTC  ACG  ATT  TTT  GCA  TAT  ATG  AAT  GAA  ACC  TCT  TCC  CGA  AAG  GAA      1038
Pro  Phe  Thr  Ile  Phe  Ala  Tyr  Met  Asn  Glu  Thr  Ser  Ser  Arg  Lys  Glu
          280                      285                      290

AAA  TGG  GAC  CTC  CAA  GCT  CTT  AGG  TTT  TTA  TCA  ATT  AAT  TCA  ATA  ATT      1086
Lys  Trp  Asp  Leu  Gln  Ala  Leu  Arg  Phe  Leu  Ser  Ile  Asn  Ser  Ile  Ile
295                           300                      305                     310

GAC  CCT  TGG  GTC  TTT  GCC  ATC  CTT  AGG  CCT  CCT  GTT  CTG  AGA  CTA  ATG      1134
Asp  Pro  Trp  Val  Phe  Ala  Ile  Leu  Arg  Pro  Pro  Val  Leu  Arg  Leu  Met
                         315                      320                      325

CGT  TCA  GTC  CTC  TGT  TGT  CGG  ATT  TCA  TTA  AGA  ACA  CAA  GAT  GCA  ACA      1182
Arg  Ser  Val  Leu  Cys  Cys  Arg  Ile  Ser  Leu  Arg  Thr  Gln  Asp  Ala  Thr
               330                      335                      340

CAA  ACT  TCC  TGT  TCT  ACA  CAG  TCA  GAT  GCC  AGT  AAA  CAG  GCT  GAC  CTT  TG  1232
Gln  Thr  Ser  Cys  Ser  Thr  Gln  Ser  Asp  Ala  Ser  Lys  Gln  Ala  Asp  Leu
          345                      350                      355

AGGTCAGTAG   TTTAAAAGTT   CTTAGTTATA   TAGCATCTGG   AAGATCATTT   TGAAATTGTT      1292

CCCTGGAGAA   ATGAAAACAG   TGTGTAAACA   AAATGAAGCT   GCCCTAATAA   AAGGAGTAT       1352

ACAAACATTT   AAGCTGTGGT   CAAGGCTACA   GATGTGCTGA   CAAGGCACTT   CATGTAAAGT      1412

GTCAGAAGGA   GCTACAAAAC   CTACCCTCAA   TGAGCATGGT   ACTTGGCCTT   TGGAGGAACA      1472

ATCGGCTGCA   TTGAAGATCC   AGCTGCCTAT   TGATTTAAGC   TTTCCTGTTG   AATGACAAAG      1532

TATGTGGTTT   TGTAATTTGT   TTGAAACCCC   AAACAGTGAC   TGTACTTTCT   ATTTTAATCT      1592

TGCTACTACC   GTTATACACA   TATAGTGTAC   AGCCAGACCA   GATTAAACTT   CATATGTAAT      1652
```

```
CTCTAGGAAG  TCAATATGTG  GAAGCAACCA  AGCCTGCTGT  CTTGTGATCA  CTTAGCGAAC   1712

CCTTTATTTG  AACAATGAAG  TTGAAAATCA  TAGGCACCTT  TTACTGTGAT  GTTTGTGTAT   1772

GTGGGAGTAC  TCTCATCACT  ACAGTATTAC  TCTTACAAGA  GTGGACTCAG  TGGGTTAACA   1832

TCAGTTTTGT  TTACTCATCC  TCCAGGAACT  GCAGGTCAAG  TTGTCAGGTT  ATTTATTTTA   1892

TAATGTCCAT  ATGCTAATAG  TGATCAAGAA  GACTTTAGGA  ATGGTTCTCT  CAACAAGAAA   1952

TAATAGAAAT  GTGTCAAGGC  AGTTAATTCT  CATTAATACT  CTTATTATCC  TATTTCTGGG   2012

GGAGGATGTA  CGTGGCCATG  TATGAAGCCA  AATATTAGGC  TTAAAAACTG  AAAAATCTGG   2072

TTCATTCTTC  AGATATACTG  GAACCCTTTT  AAAGTTGATA  TTGGGGCCAT  GAGTAAAATA   2132

GATTTTATAA  GATGACTGTG  TTGTACCAAA  ATTCATCTGT  CTATATTTTA  TTTAGGGGAA   2192

CATGGTTTGA  CTCATCTTAT  ATGGGAAACC  ATGTAGCAGT  GAGTCATATC  TTAATATATT   2252

TCTAAATGTT  TGGCATGTAA  ATGTAAACTC  AGCATCAAAA  TATT                     2296
```

(2) INFORMATION FOR SEQ ID NO:4:

(i) SEQUENCE CHARACTERISTICS:
        (A) LENGTH: 358 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:4:

```
Met  Gly  Asn  Ala  Ser  Asn  Asp  Ser  Gln  Ser  Glu  Asp  Cys  Glu  Thr  Arg
 1                  5                       10                      15

Gln  Trp  Leu  Pro  Pro  Gly  Glu  Ser  Pro  Ala  Ile  Ser  Ser  Val  Met  Phe
             20                       25                      30

Ser  Ala  Gly  Val  Leu  Gly  Asn  Leu  Ile  Ala  Leu  Ala  Leu  Leu  Ala  Arg
         35                       40                      45

Arg  Trp  Arg  Gly  Asp  Val  Gly  Cys  Ser  Ala  Gly  Arg  Arg  Ser  Ser  Leu
     50                       55                      60

Ser  Leu  Phe  His  Val  Leu  Val  Thr  Glu  Leu  Val  Phe  Thr  Asp  Leu  Leu
65                       70                      75                      80

Gly  Thr  Cys  Leu  Ile  Ser  Pro  Val  Val  Leu  Ala  Ser  Tyr  Ala  Arg  Asn
                     85                      90                      95

Gln  Thr  Leu  Val  Ala  Leu  Ala  Pro  Glu  Ser  Arg  Ala  Cys  Thr  Tyr  Phe
             100                      105                     110

Ala  Phe  Ala  Met  Thr  Phe  Phe  Ser  Leu  Ala  Thr  Met  Leu  Met  Leu  Phe
         115                      120                     125

Ala  Met  Ala  Leu  Glu  Arg  Tyr  Leu  Ser  Ile  Gly  His  Pro  Tyr  Phe  Tyr
     130                      135                     140

Gln  Arg  Arg  Val  Ser  Arg  Ser  Gly  Gly  Leu  Ala  Val  Leu  Pro  Val  Ile
145                      150                     155                     160

Tyr  Ala  Val  Ser  Leu  Leu  Phe  Cys  Ser  Leu  Pro  Leu  Leu  Asp  Tyr  Gly
                     165                     170                     175

Gln  Tyr  Val  Gln  Tyr  Cys  Pro  Gly  Thr  Trp  Cys  Phe  Ile  Arg  His  Gly
             180                      185                     190

Arg  Thr  Ala  Tyr  Leu  Gln  Leu  Tyr  Ala  Thr  Leu  Leu  Leu  Leu  Leu  Ile
```

|     |     |     |     |     | 195 |     |     |     |     | 200 |     |     |     |     | 205 |
|-----|-----|-----|-----|-----|-----|-----|-----|-----|-----|-----|-----|-----|-----|-----|-----|

Val Ser Val Leu Ala Cys Asn Phe Ser Val Ile Leu Asn Leu Ile Arg
    210                 215                 220

Met His Arg Arg Ser Arg Arg Ser Arg Cys Gly Pro Ser Leu Gly Ser
225                 230                 235                 240

Gly Arg Gly Gly Pro Gly Ala Arg Arg Arg Gly Glu Arg Val Ser Met
                245                 250                 255

Ala Glu Glu Thr Asp His Leu Ile Leu Leu Ala Ile Met Thr Ile Thr
            260                 265                 270

Phe Ala Val Cys Ser Leu Pro Phe Thr Ile Phe Ala Tyr Met Asn Glu
        275                 280                 285

Thr Ser Ser Arg Lys Glu Lys Trp Asp Leu Gln Ala Leu Arg Phe Leu
    290                 295                 300

Ser Ile Asn Ser Ile Ile Asp Pro Trp Val Phe Ala Ile Leu Arg Pro
305                 310                 315                 320

Pro Val Leu Arg Leu Met Arg Ser Val Leu Cys Cys Arg Ile Ser Leu
                325                 330                 335

Arg Thr Gln Asp Ala Thr Gln Thr Ser Cys Ser Thr Gln Ser Asp Ala
            340                 345                 350

Ser Lys Gln Ala Asp Leu
        355

( 2 ) INFORMATION FOR SEQ ID NO:5:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:5:

GATGAGCTCT TTAAAAGGAG GGCGCATCTC TTTTCCAGG     39

( 2 ) INFORMATION FOR SEQ ID NO:6:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( v ) FRAGMENT TYPE:

( v i ) ORIGINAL SOURCE:

( x i ) SEQUENCE DESCRIPTION: SEQ ID NO:6:

GGTGAACACC AGCTCGGT     18

( 2 ) INFORMATION FOR SEQ ID NO:7:

-continued (i) SEQUENCE CHARACTERISTICS:
  (A) LENGTH: 18 base pairs
  (B) TYPE: nucleic acid
  (C) STRANDEDNESS: single
  (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:7:

CTTACCTGCA GCTGTACG    18

(2) INFORMATION FOR SEQ ID NO:8:

(i) SEQUENCE CHARACTERISTICS:
    (A) LENGTH: 18 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (iv) ANTI-SENSE: YES (v) FRAGMENT TYPE:

(vi) ORIGINAL SOURCE:

(xi) SEQUENCE DESCRIPTION: SEQ ID NO:8:

GATGGCAAAG ACCCAAGG    18

(2) INFORMATION FOR SEQ ID NO:9:

(i) SEQUENCE CHARACTERISTICS:
    (A) LENGTH: 32 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:9:

ATCTGGCACC ACACCTTCTA CAAGTAGCTG CG    32

(2) INFORMATION FOR SEQ ID NO:10:

(i) SEQUENCE CHARACTERISTICS:
    (A) LENGTH: 32 base pairs
    (B) TYPE: nucleic acid
    (C) STRANDEDNESS: single
    (D) TOPOLOGY: linear (ii) MOLECULE TYPE: cDNA (iii) HYPOTHETICAL: NO -continued ( i v ) ANTI-SENSE: YES ( v ) FRAGMENT TYPE:

( v i ) ORIGINAL SOURCE:

( x i ) SEQUENCE DESCRIPTION: SEQ ID NO:10:

CGTCATACTC CTGCTTGCTG ATCCACATCT GC  32